United States Patent [19]
Paradise

[11] Patent Number: 5,795,573
[45] Date of Patent: Aug. 18, 1998

[54] HOMEOPATHIC PHARMACEUTICAL COMPOSITIONS

[76] Inventor: Lou Paradise, 7 Hook Rd., Rhinebeck, N.Y. 12572

[21] Appl. No.: 4,573

[22] Filed: Jan. 8, 1998

[51] Int. Cl.⁶ .................... A61K 33/44; A61K 35/00; A01N 65/00
[52] U.S. Cl. .................... 424/195.1; 424/78.05; 424/125; 424/447; 424/DIG. 13; 602/48
[58] Field of Search ................ 424/195.1, 78.05, 424/125, DIG. 13, 78.06, 447; 602/48

[56] References Cited

U.S. PATENT DOCUMENTS

| | | | |
|---|---|---|---|
| 4,684,522 | 8/1987 | Marissal et al. | 424/195.1 |
| 5,006,338 | 4/1991 | Luenemann | 424/195.1 |
| 5,162,037 | 11/1992 | Whitson-Fischman | 600/12 |

OTHER PUBLICATIONS

APS Abstract Japanese Patent 08–73340 Maeda et al "Skin External Preparation" Mar. 19, 1996.
Derwent Abstract AN97–255463/23 JP09087189 Ichimaru Pharcos Inc. Mar. 3, 1997.
Derwent Abstract AN91–133906/19 Gavarelli "Homeophathic pharmaceutical. . . " DE3936046 May 2, 1991.
ACS CASM Abstract CA080–019402(04) Hiroshi et al JP73005022 "Skin cosmetics containing *Aesculus hippocastanum* extract" Kuriyma et al. Feb. 13, 1973.

*Primary Examiner*—Herbert J. Lilling
*Attorney, Agent, or Firm*—John Lezdey

[57] ABSTRACT

A homeopathic topical anti-inflammatory and pain relieving composition containing an effective amount of the combination of Arnica Montana, *Rhus toxicodendron* and *Aesculus hippocastanum* together with belladonna in the form of a lotion, cream or gel.

19 Claims, No Drawings

HOMEOPATHIC PHARMACEUTICAL COMPOSITIONS

FIELD OF THE INVENTION

The present invention relates to homeopathic topical anti-inflammatory and pain relieving compositions. More particularly, there is provided a composition which contains a synergistic combination of extracts from Arnica Montana, *Rhus toxicodendron* and *Aesculus hippocastanum* and belladonna.

BACKGROUND OF THE INVENTION

Many analgesic topical compositions for treating muscular cramps, soreness and pain contain irritants and counter-irritants. These ingredients are odorous, irritate the skin and do not treat all the symptoms or causes of pain. In order to relieve pain in many inflammatory injuries or diseases it is desirable to promote healing, improve circulation to tissues nerves, provide anti-inflammatory activity, and mask pain caused by kinins and kallakreins. Many injuries have a multiplicity of symptoms which require a cocktail of ingredients in order to provide relief. However, many combinations of active ingredients do not act in concert to provide relief or they conflict with each other so that only one of the ingredients is effective.

Furthermore, it is desirable to obtain deep penetration of the active ingredients so as to induce the proper cytokines to provide the proper response to cause healing of the injury or inflammation. It is further desirable to provide an analgesic which does not rely upon counter-irritants that act by causing a superficial inflammation on the skin, which deadons the sensation of pain perceived by the sensory organ and only masks the pain.

It is desirable to relax soft tissues, vasodilate blood vessels which are vasoconstricted so as to allow blood to flow normally, returning nutrients and oxygen to areas to promote healing. It is also desirable to release nerves which have been entrapped by hypercontraction of muscle tissue.

U.S. Pat. No. 5,162,037 to Whitson-Fischman discloses a method for treating pathogenic conditions of the body by preparing a homeopathic mixture of at least one herb or herbal extract which exhibits therapeutic property and add a magnetically permeable substance to the mixture, magnetize the mixture and administer the composition orally, topically or by injection. The herbs include Arnica Montana, Rhus Toxicum, pineal gland and others but does not include belladonna or others which are antispasm or promote circulation by topical application.

U.S. Pat. No. 4,684,522 to Marissal et al discloses a slendering and anti-cellulitis composition which contains extract of Arnica Montana L and extracts of plants containing saponins which includes *Aesculus hippocastanum* L together with the extract of Kola nut.

SUMMARY OF THE INVENTION

According to the invention, there is provided a topically applied composition and method of treating patients suffering from pain and inflammation. The invention provides a composition comprising:

A. an effective amount of a composition of herbs or extras of herbs consisting of Arnica Montana, *Rhus toxicodendron* and *Aesculus hippocastanum*, and B. an effective amount of belladonna, in a pharmaceutically acceptable carrier to form a lotion, cream or gel.

Advantageously, the composition includes an aid to help in penetration, for example, a surfactant.

Preferably, the composition contains skin conditioning components such as graphite and trace minerals.

It has been found to be advantageous to place a composition of the invention on an occlusive bandage in order to obtain deeper penetration of the effective ingredients. The occlusive bandage is particularly useful when the patient is continuing participation in sports and need continuing relief.

DESCRIPTION OF THE PREFERRED EMBODIMENTS

According to the invention, there is provided a topically applied composition for treating a patient suffering from inflammation and/or pain resulting from a disease or injury. The composition can be in the form of a lotion, cream or gel and applied as a rub or in combination with an occlusive bandage. It has been found that a therapeutically effective amount of the combination of herbs or extracts of Arnica Montana, *Rhus toxicodendron* and *Aesculus hippocastanum* together with belladonna provides relief from pain, cramping and inflammation.

Although greater amounts of the ingredients can be used in the composition it has been found that about 2 to 10% by weight of the combination of herbs or herbal extracts is effective. The combination can comprise about 1 to 5% by weight of Arnica Montana, about 1 to 5% by weight of Rhus toxicodendron and about 0.5 to 3% by weight of *Aesculus hippocastanum*.

There appears to be a synergistic effect when about 0.5 to 5% by weight of belladonna is used with the combination although greater amounts can also be used, if desired.

The Arnica Montana by itself has been used to provide relief from shock and trauma to the muscle. However, by itself it cannot cover the full spectrum of pain or inflammation to the body.

The *Rhus toxicodendron* is by itself useful for sprains, arthritic pain and backaches but not for cramps or muscle soreness.

*Aesculus hippocastanum* is particularly useful by itself for leg pain.

However, when the extracts are combined with belladonna, it has been found that the combination can be applied to all parts of the body and treat all types of inflammations and pains resulting from trauma or disease without interfering with other medications that the patient may be using or providing a concern because of pregnancy.

The compositions of the invention can be used in combination with other herbs or herbal extracts. For example, it may be desirable to thin the blood or to better promote circulation such as Naja and *Crotalus horridum*.

To condition the skin graphite and/or trace minerals such as copper and zinc salts may be included.

Anti-inflammatory agents such as Echinacea Angustifolia and Lachesis Ninta that contains enzymes which relieves muscle tightness and cramps can be included in the composition.

The combinations as used herein stimulates the body's self healing mechanism by promoting circulation in the micro-capillary system. This restores blood flow to the inflammed areas where most of the pain is realized. When blood flow is improved to an ailing joint, healing begins and true pain relief is realized.

The compositions of the invention may include other plant or herbal extracts. For example, there may be utilized extracts of Paraguay tea, Kola and Guarana which provide a source of methylxanthines, saponius, tannins and glycosides which have been shown to reduce swelling and redness. The extract of Paraguay tea is known as "Mate extract" and is described in the "International Cosmetic Ingredient Dictionary", 5th Edition. Mate extract is commercially available in combination with extracts of Kola and Guarana which is sold by Cosmetic Ingredient Resources of Stamford, Conn. under the trademark "QUENCHT."

Suitable herbs which can be used also include symphytum, officianalis, *Moschus moscheferous*, *Cow bezoar*, *Pripalia geniculata*, *Plantago asiatica*, Causticum, *Helianthemum canadense*, *Ornithogalum umbellatum*, *Clematis crispa*, *Impatiens pallida*, Prunus Cerasus, and the like.

A surfactant can be included in the composition so as to provide deeper penetration of the ingredients. Although natural surfactants are preferred, others such as isopropyl myristate can be used.

Other ingredients may be used, preferably, in amounts from about 0.5 to 2% by weight.

The following examples illustrating the compositions of the invention are not intended to limit the scope of the invention. The amounts indicated are by weight percent unless otherwise noted.

EXAMPLE 1

A gel is prepared by admixing the following ingredients.

| Ingredient | Wt % |
| --- | --- |
| Carbomer 940 | 2.10 |
| Xantham gum | 0.15 |
| Propylene glycol | 51.94 |
| Dipropylene glycol | 10.00 |
| Ethoxydiglycol | 15.00 |
| Dimethylisosorbide | 10.00 |
| Aloe Vera gel | 2.00 |
| Surfactant | 0.05 |
| Arnica Montana | 2.50 |
| Belladona | 2.50 |
| Rhus toxicodendron | 2.00 |
| Aesculus hippocastanum | 1.76 |
|  | 100.00 |

EXAMPLE 2

A creme was formed by admixing the following ingredients:

| Ingredient | Wt |
| --- | --- |
| *Aesculus hippocastanum* extract | 6 mcg/g |
| Arnica Montana extract | 6 mcg/g |
| Belladonna | 6 mcg/g |
| *Echinacea angustifolia* extract | 6 mcg/g |
| *Rhus toxicodendron* extract | 6 mcg/g |
| *Ruta graveoleus* extract | 6 mcg/g |
| Graphites | 6 mcg/g |
| *Crotalus horridus* extract | 0.08 mcg/g |

| Ingredient | Wt |
| --- | --- |
| *Heloderma horridum* extract | 0.08 mcg/g |
| Lachesis extract | 0.08 mcg/g |
| Naja extract | 0.08 mcg/g |
| Isopropyl myristate | 30 mg/g |
| Brij 72 | 2 mg/g |
| Brij 721S | 2 mg/g |
| Water | 83 mg/g |
| Methyl paraben | 0.2 mg/g |
| Propyl paraben | 20 mcg/g |
| Glycerine | 3 mg/g |
| 20% NaOH | 0.5 mg/g |
| Dowcil 200 | 50 mcg/g |
| Akodel 112 | 2 mg/g |

The creme may be placed on a gauze to be placed on an adhesive plastic tape to form an occlusive bandage.

EXAMPLE 3

A lotion is prepared by admixing the following ingredients:

| Ingredient | Wt % |
| --- | --- |
| Belladonna | 1.10 |
| Propylene Glycol Stearate | 6.50 |
| Isocetyl alcohol | 5.00 |
| PEG-100 Stearate | 1.20 |
| Water | 69.90 |
| *Rhus toxicodendron* | 3.00 |
| Methyl paraben | 0.20 |
| Propylene glycol | 12.00 |
| Sorbitan palmitate | 0.60 |
| Arnica Montana | 3.00 |
| *Aesculus hippocastanum* | 3.00 |
| Mate extract | 0.50 |
|  | 100% |

What is claimed is:

1. A homeopathic topically applied composition for treating a patient for inflammation and pain which comprises:
   A. an effective amount of a combination of herbs or extracts of Arnica Montana, *Rhus toxicodendron* and *Aesculus hippocastanum*, and
   B. an effective amount of belladona, in pharmaceutically acceptable carrier to form a lotion, cream or gel.

2. The composition of claim 1 including a surfactant.

3. The composition of claim 1 wherein said combination of herbs or extracts comprises about 2 to 10% by weight of said composition.

4. The composition of claim 1 wherein said belladona comprises about 0.5 to 5% by weight of said composition.

5. The composition of claim 1 comprising about 1 to 5% by weight of Arnica Montana, about 1 to 5% by weight of said *Rhus toxicodendron* and 0.5 to 3% by weight of aesculus hippocastanum.

6. The composition of claim 1 comprising about 0.5 to 10% by weight of belladona.

7. The composition of claim 1 including an effective amount of graphite.

8. The composition of claim 1 including an effective amount of glucosamine.

9. The composition of claim 1 including a therapeutically effective amount of an herb or herb extract selected from the group consisting of naja, crotalus, echinacea, ruta and mixtures thereof.

10. The composition of claim 1 including a therapeutically effective amount of lachesis muta.

11. The composition of claim 1 including an effective amount of minerals.

12. The composition of claim 1 including an effective amount of an extract of Peruvian tea.

13. The composition of claim 1 in combination with an occlusive bandage.

14. A homeopathic topically applied cream or lotion comprising a therapeutically effective amount of
   A. an herb or herb extract of *Aesculus hippocastanum*, Arnica Montana, echinacea angustifolia, *Rhus toxicodendron*, *Ruta graveoleus*, *Crotalus horridus*, *Heloderma horridum*, an naja;
   B. graphites; and
   C. lachesis.

15. The cream or lotion of claim 14 including a surfactant.

16. A method of treating a patient suffering from pain or inflammation which comprises topically administering to said patient the composition of claim 1 to the site of pain or inflammation.

17. A method of treating of claim 5 to the site of pain or inflammation.

18. The method of treating of claim 9 to the site of pain or inflammation.

19. A method of treating a patient suffering pain or inflammation which comprises administering to the site of pain or inflammation the combination of claim 13.

\* \* \* \* \*